(12) United States Patent
Secatch et al.

(10) Patent No.: US 11,017,127 B2
(45) Date of Patent: May 25, 2021

(54) STORAGE COMPUTE APPLIANCE WITH INTERNAL DATA ENCRYPTION

(71) Applicant: Seagate Technology LLC, Cupertino, CA (US)

(72) Inventors: Stacey Secatch, Longmont, CO (US); Kristofer C. Conklin, Burnsville, MN (US); Dana Lynn Simonson, Owatonna, MN (US); Robert Wayne Moss, Windsor, CO (US)

(73) Assignee: Seagate Technology LLC, Fremont, CA (US)

( * ) Notice: Subject to any disclaimer, the term of this patent is extended or adjusted under 35 U.S.C. 154(b) by 161 days.

(21) Appl. No.: 15/885,187

(22) Filed: Jan. 31, 2018

(65) Prior Publication Data

US 2019/0236318 A1 Aug. 1, 2019

(51) Int. Cl.
| | |
|---|---|
| *G06F 21/78* | (2013.01) |
| *H04L 29/06* | (2006.01) |
| *G06F 3/06* | (2006.01) |
| *H04L 9/08* | (2006.01) |
| *H04L 9/14* | (2006.01) |
| *G16H 10/60* | (2018.01) |
| *G06F 16/50* | (2019.01) |

(52) U.S. Cl.
CPC ............ *G06F 21/78* (2013.01); *G06F 3/0629* (2013.01); *G06F 3/0679* (2013.01); *H04L 9/08* (2013.01); *H04L 9/088* (2013.01); *H04L 9/0891* (2013.01); *H04L 9/0894* (2013.01); *H04L 9/14* (2013.01); *H04L 63/0428* (2013.01); *G06F 16/50* (2019.01); *G16H 10/60* (2018.01); *H04L 2209/88* (2013.01)

(58) Field of Classification Search
CPC ...... G06F 21/78; G06F 3/0629; G06F 3/0679; G06F 16/50; G06F 4129/06; H04L 9/14; H04L 9/088; H04L 9/0894; H04L 9/0891; H04L 9/08; H04L 63/0428; H04L 2209/88; H04L 29/06; G16H 10/60
USPC .......................................................... 713/193
See application file for complete search history.

(56) References Cited

U.S. PATENT DOCUMENTS

| | | |
|---|---|---|
| 5,646,993 A | 7/1997 | Alzawa |
| 6,993,195 B2 | 1/2006 | Olivieri |
| 7,227,952 B2 | 6/2007 | Qawami et al. |
| 7,302,571 B2 | 11/2007 | Noble et al. |
| 7,330,957 B2 | 2/2008 | Miyazaki |
| 7,380,140 B1 | 5/2008 | Weissman et al. |
| 7,743,409 B2 | 6/2010 | Gonzalez et al. |

(Continued)

*Primary Examiner* — Ashokkumar B Patel
*Assistant Examiner* — Quazi Farooqui
(74) *Attorney, Agent, or Firm* — Hall Estill Attorneys at Law

(57) ABSTRACT

Method and apparatus for managing data in a data storage device configured as a storage compute appliance. In some embodiments, the data storage device has a non-volatile memory (NVM) and a controller circuit. The NVM stores a plurality of data sets encrypted by at least one encryption key. The controller circuit performs a storage compute appliance process by locally decrypting the plurality of data sets in a local memory of the data storage device, generating summary results data from the decrypted data sets, and transferring the summary results data across the host interface to an authorized user without a corresponding transfer of any portion of the decrypted data sets across the host interface.

20 Claims, 5 Drawing Sheets

(56) References Cited

U.S. PATENT DOCUMENTS

| | | |
|---|---|---|
| 7,844,711 B2 | 11/2010 | Kobayashi |
| 8,925,100 B2 | 12/2014 | Chase |
| 9,128,745 B2 | 9/2015 | Crudele |
| 9,575,618 B2 | 2/2017 | Yamasani |
| 9,613,205 B2 | 4/2017 | Steeves et al. |
| 9,760,695 B2 | 9/2017 | Manago et al. |
| 2002/0091643 A1 | 7/2002 | Okamoto |
| 2010/0031349 A1 | 2/2010 | Bingham |
| 2011/0154443 A1 | 6/2011 | Thakur |
| 2012/0093318 A1* | 4/2012 | Obukhov .............. G06F 21/79 380/277 |
| 2012/0124183 A1 | 5/2012 | Long |
| 2012/0179908 A1* | 7/2012 | Duma ................ G16H 10/65 713/165 |
| 2015/0100412 A1* | 4/2015 | Sterns ............... G06Q 30/0251 705/14.41 |
| 2015/0227191 A1* | 8/2015 | Pitigoi-Aron ........ H04W 84/18 713/189 |
| 2015/0244710 A1* | 8/2015 | Koster ............... G06F 21/44 713/171 |
| 2015/0278260 A1 | 10/2015 | Ramos |
| 2015/0286436 A1 | 10/2015 | Olson |
| 2016/0365976 A1* | 12/2016 | Yamaguchi .......... H04L 9/0894 |
| 2017/0131902 A1 | 5/2017 | Goss |
| 2017/0237563 A1 | 8/2017 | El-Moussa |
| 2017/0264431 A1 | 9/2017 | Mattsson |
| 2018/0211033 A1 | 7/2018 | Aditham |
| 2018/0287786 A1* | 10/2018 | Calahan ................ H04L 9/083 |
| 2018/0288024 A1* | 10/2018 | Munafo ............... H04W 12/06 |
| 2020/0027014 A1 | 1/2020 | Wen |

\* cited by examiner

MEDICAL RECORDS EXAMPLE

DMV DATABASE EXAMPLE

SOLID STATE DRIVE (SSD) STORAGE COMPUTE APPLIANCE

HARD DISC DRIVE (HDD)/HYBRID DRIVE STORAGE COMPUTE APPLIANCE

STORAGE COMPUTE APPLIANCE WITH INTERNAL DATA ENCRYPTION

SUMMARY

Various embodiments of the present disclosure are generally directed to a data storage device configured as a storage compute appliance to perform data analysis on encrypted data stored by the device.

In some embodiments, the data storage device has a non-volatile memory (NVM) and a controller circuit. The NVM stores a plurality of data sets encrypted by at least one encryption key. The controller circuit performs a storage compute appliance process by locally decrypting the plurality of data sets in a local memory of the data storage device, generating summary results data from the decrypted data sets, and transferring the summary results data across the host interface to an authorized user without a corresponding transfer of any portion of the decrypted data sets across the host interface.

These and other features and advantages of various embodiments of the present disclosure can be understood from a review of the following detailed description in conjunction with the accompanying drawings.

DETAILED DESCRIPTION

Figure 1:
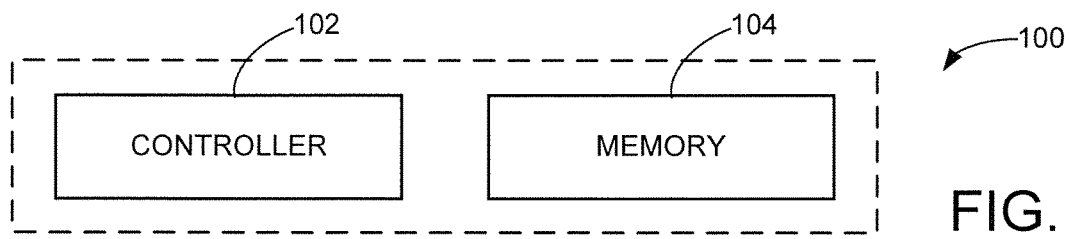
FIG. 1 is a functional block diagram of a data storage device configured and operated accordance with some embodiments.

The present disclosure is generally directed to data storage systems, and more particularly to configuring a data storage device as a storage compute appliance to securely process confidential data.

Data storage devices store and retrieve user data in a fast and efficient manner. A data storage device generally includes a top level controller circuit and a non-volatile memory (NVM). The controller circuit operates to store user data to, and retrieve the user data from, the NVM. The NVM can take any number of forms, including solid state semiconductor memory such as in the form of flash memory and rotatable recording media such as in the form of one or more rotatable magnetic recording discs.

Data security schemes are implemented in data storage devices to prevent or reduce the ability of an unauthorized party from gaining access to stored data. A variety of data security schemes have been implemented in the art, including the use of encryption. Encryption involves the application of a cryptographic algorithm to transform a set of plaintext data into ciphertext data using one or more control values such as encryption keys, seed values, counter values, etc.

In a shared storage environment, data sets from multiple owners (e.g., different users, host devices, processes, etc.) are stored on the same storage device or group of storage devices. Each data set can be encrypted using a separate encryption key to individually protect the data. This reduces the likelihood that another party can gain unauthorized access to an individual user's data set.

However, such a scheme also increases the difficulty in performing an analysis of all of the various data sets, such as in a multi-user search or calculation operation in which results from the entire group are reported to an authorized user of an analysis application on a host device. This type of scheme also increases the risk of inadvertent exposure of the underlying data.

Various embodiments are generally directed to an apparatus and method for managing data in a data storage environment. As explained below, some embodiments provide a data storage device having a controller circuit and a non-volatile memory (NVM).

The data storage device is configured as a storage compute appliance to perform internal accesses of data sets stored to the NVM. The data sets may be associated with different users and may be individually encrypted using user based encryption keys. The data sets are additionally encrypted by a storage compute appliance key. The appliance key is stored internally by the appliance and is not transferred externally by or to the storage device.

When activated, the appliance performs an internal analysis across each of the data sets by decrypting and processing the data to generate summary results data. The summary results data provide a top level summary of the analysis without revealing any of the underlying user data. The summary results data can be safely transferred by the appliance to an authorized user via a transfer outside the storage device to a separate host device. In this way, multi-user data analyses can be performed while ensuring that individual users can only access their own underlying data.

These and other features and advantages of various embodiments can be understood beginning with a review of FIG. 1 which shows a functional block representation of an exemplary data storage device 100. The device 100 includes a controller 102 and a memory 104. The controller 104 is a control circuit that provides top level control of data transfer operations between the memory 104 and a host device. The controller may be realized as a non-programmable hardware based control circuit and/or one or more programmable processors that execute programming (e.g., firmware) stored in a local memory. The memory 104 includes one or more forms of non-volatile memory (NVM) to store the user data. Examples include but are not limited to solid state semiconductor memory, rotatable memory, etc.

Figure 2:
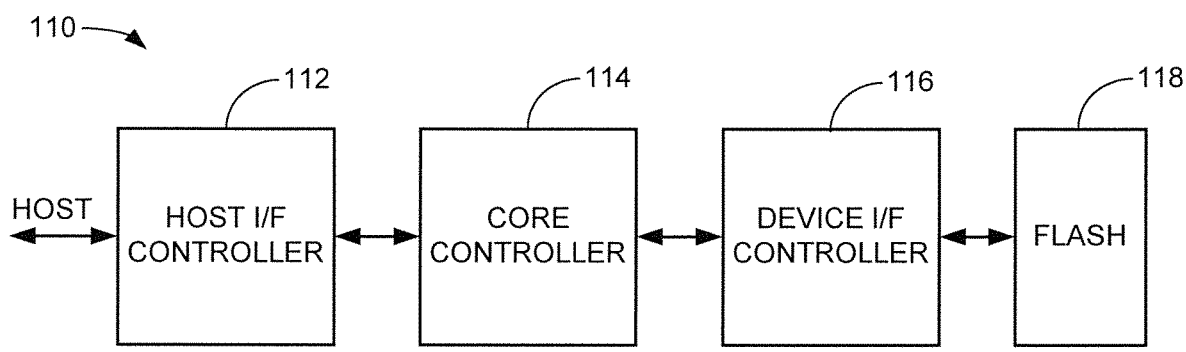
FIG. 2 is a functional block diagram of the storage device of FIG. 1 configured as a solid state drive (SSD).

FIG. 2 shows a data storage device 110 that corresponds to the data storage device 100 of FIG. 1. The device 110 is configured as a solid state drive (SSD) that uses flash memory as the NVM. This is merely for purposes of illustration and is not limiting. Other circuits and components may be incorporated into the SSD 110 as desired, but such have been omitted from FIG. 2 for purposes of clarity. The circuits in FIG. 2 may be incorporated into a single integrated circuit (IC) such as a system on chip (SOC) device, or may involve multiple connected IC devices.

The controller functions from FIG. 1 are carried out by a host interface (I/F) controller circuit 112, a core controller circuit 114 and a device I/F controller circuit 116. The host I/F controller circuit 112 may sometimes be referred to as a front end controller or processor, and the device I/F controller circuit 116 may be referred to as a back end controller or processor. Each controller 112, 114 and 116 includes a separate programmable processor with associated firmware in a suitable memory location, as well as various hardware elements, to execute data management and transfer functions. In other embodiments, a single programmable processor (or less than three programmable processors) can be configured to carry out each of the front end, core and back end processes using associated FW in a suitable memory location.

The front end controller 112 processes host communications with a host device (not separately shown). The back end controller 116 provides flash management electronics (FME) to manage data read/write/erase (R/W/E) functions with a flash memory 118. The flash memory 118 may be made up of multiple flash dies to facilitate parallel data operations. The core controller 114, also referred to as the main controller or middle controller, performs the primary data management and control for the device 110.

Figure 3:
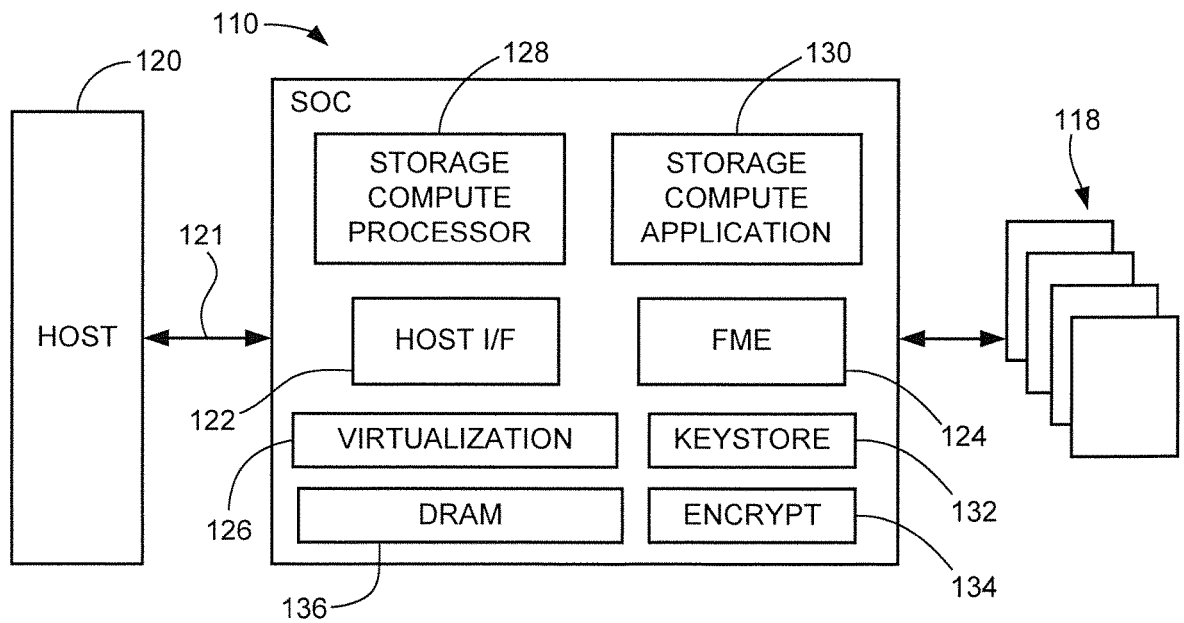
FIG. 3 illustrates aspects of the SSD of FIG. 2 configured as a storage compute appliance in some embodiments.

FIG. 3 is another functional diagram of the SSD 110 in conjunction with a host device 120. One or more suitable communication protocols are established to enable communication between the SSD 110 and the host device 120 via a host interface 121. Examples include but are not limited to PCIe, NVMe, Ethernet, SAS, etc.

Host I/F and FME blocks 122, 124 operate as described above to communicate with and transfer data between the flash memory 118 and the host 120 across the interface 121. The core controller 114 includes additional functionality including a virtualization layer 126, a storage compute processor 128 and a storage compute application 130. The virtualization layer 126 is provided for data mapping and management functions. The storage compute processor 128 executes the associated application 130 to perform specialized internal data analysis operations explained below.

A keystore 132 is a local memory that stores one or more encryption keys used by the storage compute processor 128 in conjunction with an encryption engine 134. A local volatile memory 136, such as in the form of DRAM, provides a scratch pad location to temporarily store the data utilized and generated by the storage compute processor.

The SSD 110 is selectively configured to operate as a storage compute appliance. As the term is used herein, a storage compute appliance is a specially configured data storage device having a host interface such as 121 to communicate with a separate host device such as 120. The storage device carries out internal data processing operations across multiple data sets stored by the NVM of the device to generate summary results data that are shared with an authorized user across the host interface. The decryption of the user data sets is carried out internally by the storage compute appliance and no copies of the decrypted data, decryption keys, etc. are transferred across or available from the host interface.

The data sets in the NVM (e.g., flash 118) are protected by one or more encryption keys in the internal keystore 132 to which only the storage compute processor can gain access. The keystore may be an internal memory (buffer, OTC fuses, etc.) within the integrated circuit package of the storage compute processor to limit the ability of an attacker from gaining access to the various encryption keys stored therein. The encryption engine 134 can form a portion of the storage compute application functionality and can thus be implemented via firmware, or can be a separate hardware circuit. The local memory 136 can be a portion of an existing memory of the SSD 110, such as a readback cache buffer, or can be an internal memory of the SOC device dedicated for utilization by the storage compute processing routine.

Figure 4:
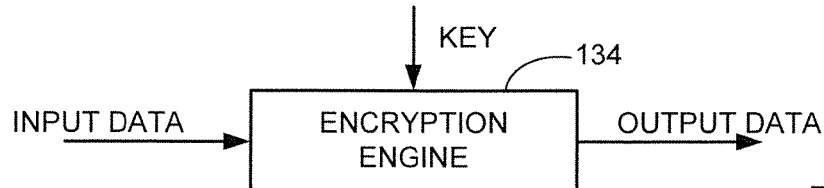
FIG. 4 shows an arrangement of a flash memory of the SSD into separate user bands.

FIG. 4 shows the encryption engine 134 in greater detail. As will be appreciated, the encryption engine utilizes a symmetric key to apply a selected cryptographic algorithm (e.g., encryption function) to transform in input plaintext data into output ciphertext data. It will be appreciated that the input plaintext data may be have been previously encrypted by an upstream encryption process, so that multiple layers of encryption/decryption can be successively applied to the data as desired. A symmetric key enables the encrypted ciphertext to be subsequently presented to the encryption engine which will use the key to return the original plaintext. Any number of different encryption functions can be used. Other encryption can be applied as well such as hashes, HMAC values, digital signatures, etc.

Figure 5:
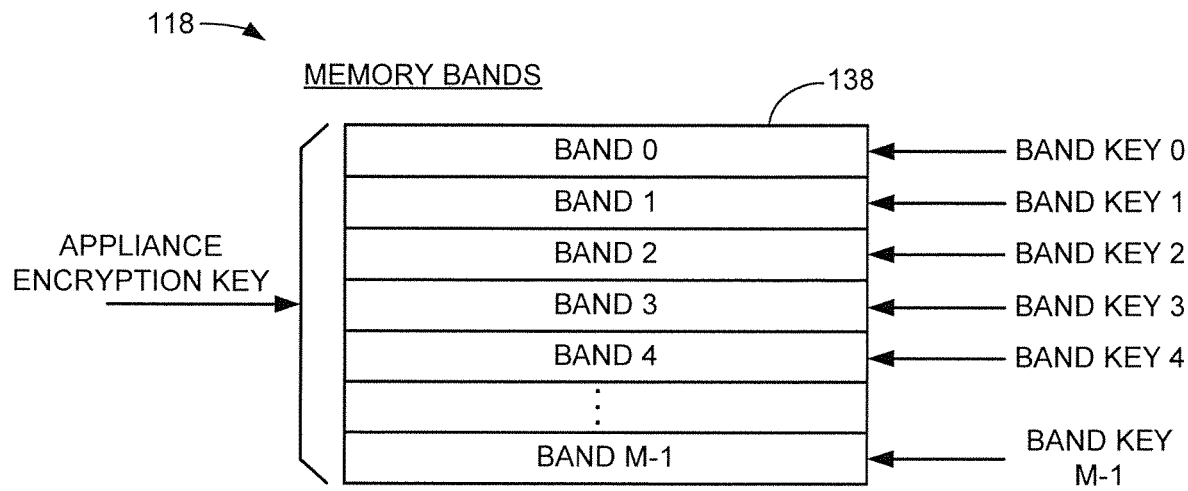
FIG. 5 is a sequence diagram illustrating operations that may be carried out by the storage compute appliance in some embodiments.

FIG. 5 is a representation of the flash memory 118 arranged into a plural number M bands 138. Other logical and/or physical arrangements of the memory can be used. Generally, each band 138 represents a selected portion of the total storage capability of the flash memory 118. Each band can be the same size, or the bands can be allocated with different storage capacities. While not limiting, it is contemplated that in at least some cases each band can be assigned to a different user (and/or host) in a shared storage device environment.

The data stored in each band can be encrypted using a separate encryption key, such as exemplified by band keys 0 to M-1. Additionally, all of the data in each band is further encrypted using a storage compute appliance encryption key. These respective keys may be stored and maintained in the keystore 132 in FIG. 3 and used by the engine 134 in FIG. 4 as needed.

Figure 6:
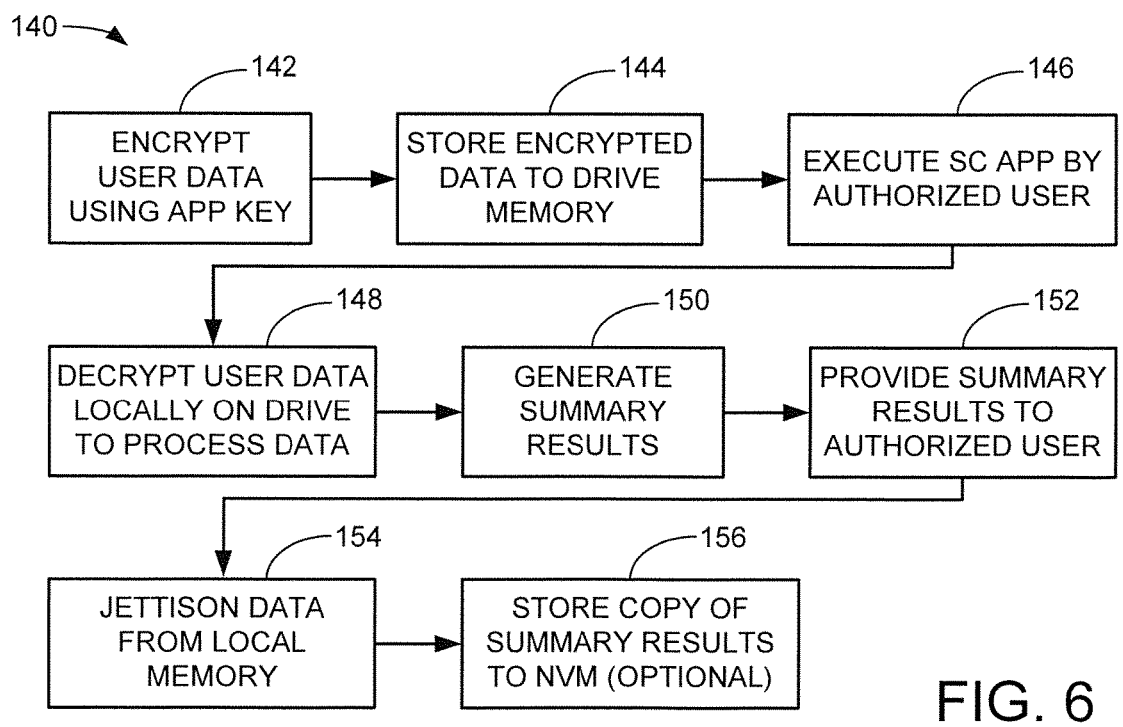
FIG. 6 illustrates an encryption engine circuit of the storage compute appliance.

FIG. 6 is a flow diagram 140 for a storage compute process carried out by the SSD 110 upon data stored in the NVM 118 as depicted in FIG. 4. The process commences with the storage of encrypted user data to the various bands. This includes encryption of the data using one or more encryption keys, including the appliance key as shown by block 142, and storage of the encrypted data as shown by block 144.

The storage compute appliance is activated at block 146 such as by the transfer of an appropriate command across the host interface 121 by an authorized user. At block 148, the appliance locally retrieves and decrypts the data from the respective bands 138 to the local memory location 136 and performs a data analysis upon the retrieved data. This results in the generation of summary results data at block 150. The summary results data are also stored in the local memory location, and are subsequently transferred across the host interface 121 to the host device 120 for review and use by the authorized user at block 152.

The decrypted user data and summary results data are thereafter jettisoned from the local memory at block 154. In this way, the unencrypted user data sets are not retained or made available for discovery by an attack upon the system. A copy of the summary results data can be encrypted and stored to the NVM 118 for future reference, as shown by optional block 156. The stored copy of the summary results data may be appended with metadata associated with the storage compute operation, such as a time/date stamp, identification of the requesting host/user, etc.

The processing type and the fowl of the summary results data will vary depending on the requirements of a given application. Whatever the form, minimal or no personally identifying information will be included in the summary results data, so that the authorized user is not made privy to the underlying user data sets.

Figure 7:
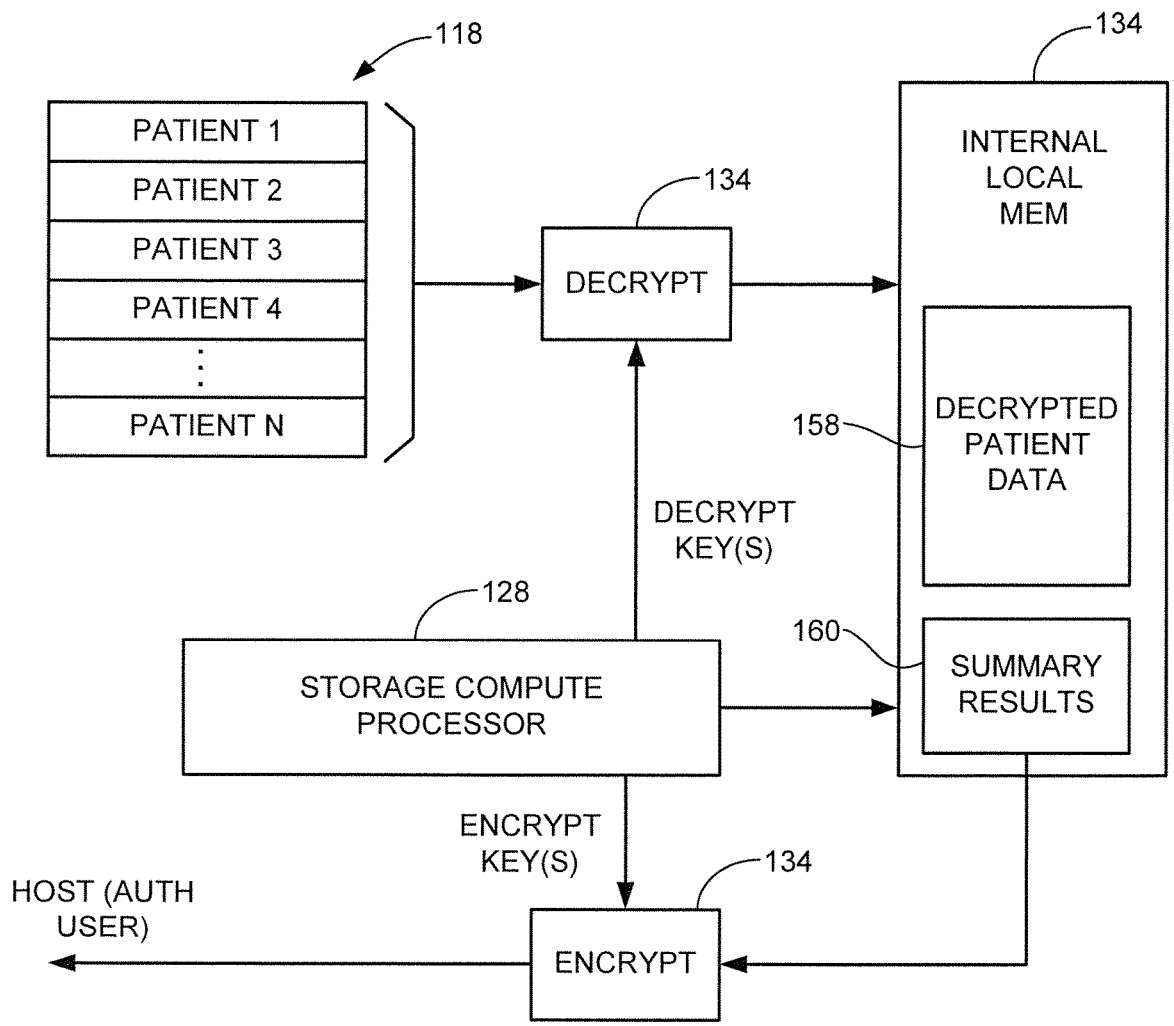
FIG. 7 is a functional block diagram showing the processing of medical records by the storage compute appliance in one illustrative example.

FIG. 7 provides an illustrative example for the SSD 110 used as a storage compute appliance in a medical records analysis environment. It is contemplated that the NVM of the storage device stores detailed medical records for a number N patients associated with a drug trial. Rather than allowing anyone to have access to the confidential details for each of the patents by exporting the data to the host, the host is only permitted to review collated data in order to look for drug interactions, correlations for efficacy, etc.

As shown by the diagram, the encrypted patient records are retrieved from the NVM 118, decrypted by the engine 134 and accumulated as a block of plaintext (decrypted) patient data 158 in the internal local memory 138 of the SSD 110. The storage compute processor 128 processes the patient data 158 to generate summary results data 160 which are also stored in the internal local memory 134. The summary results data 160 may further be encrypted as desired, and supplied to the authorized user via the host device as well as stored to the NVM 118.

In this example, if the confidential detailed records are needed at a later point in order to set up a randomized follow-up trial or similar action, a trusted administrator could be granted access to the patient data. Similarly, the patients may be able to individually request and receive their own individual records. The researchers running the correlation application do not need access to the raw patient data, and are prevented from gaining inadvertent access to these records. Moreover, because the decryption and processing is carried out internally by the SSD 110, attacks upon the host interface 121 (FIG. 3) will not yield useful data unmasking or side channel information since only the summary results data are transferred over the interface.

Figure 8:
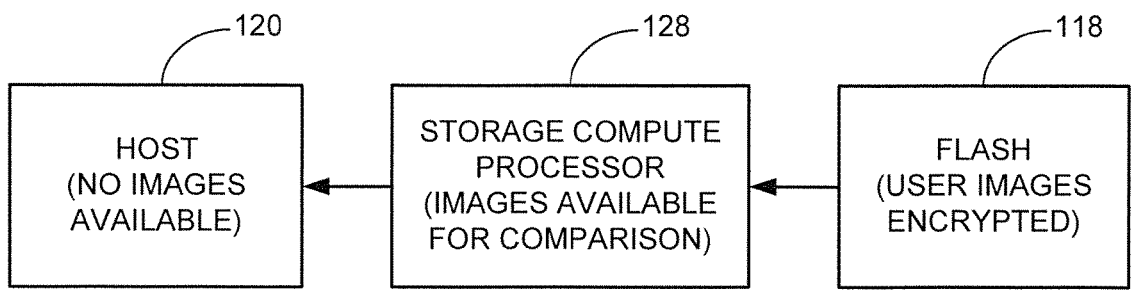
FIG. 8 is a functional block diagram showing the processing of government records by the storage compute appliance in another illustrative example.

FIG. 8 provides another illustrative example case in which government based records are maintained by the SSD 110. In this case, the government records are of the "DMV" type (e.g., department of motor vehicles) and may include personally identifying information such as name, address, organ donor status, photograph(s), signature(s), etc.

Similar processing is carried out as described above in FIG. 7, but in this case the storage compute appliance performs a facial recognition analysis upon the decrypted and internally maintained image data. The user images remain stored in encrypted form in the NVM 118. The images are accessed and processed by the storage compute processor 128 for comparison. Only output data that does not include the actual images are reported to the host 120. It will be appreciated that any number of different types of analyses can be carried out on the confidential data stored in the NVM by the storage compute process.

Figure 9:
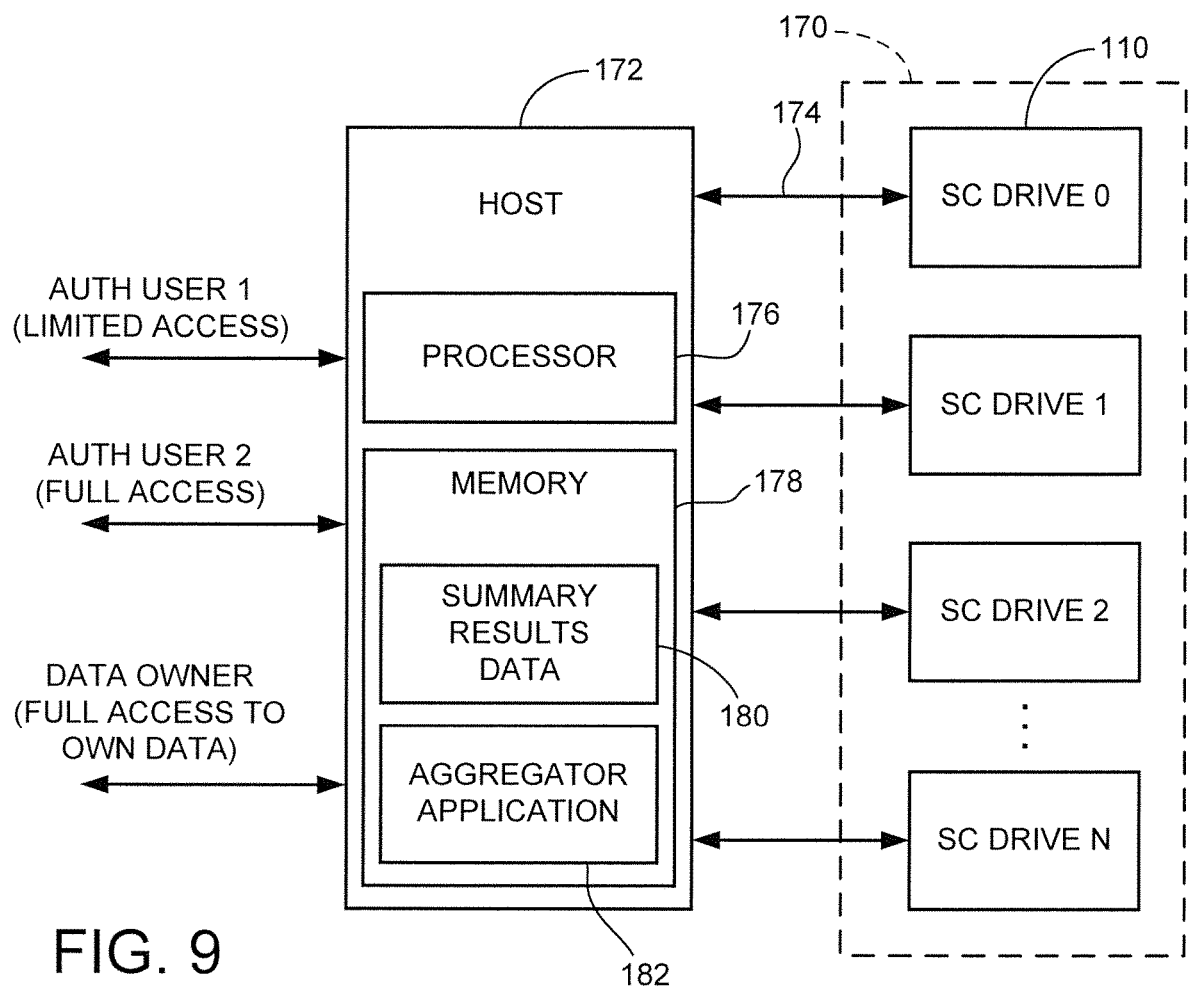
FIG. 9 is another embodiment in which multiple storage compute appliances are utilized in tandem to process data in further embodiments.

The embodiments discussed thus far have contemplated the use of a single data storage device as a storage compute appliance. Other embodiments involve the aggregation of a number of storage compute appliances to perform similar analyses. FIG. 9 shows a multi-storage device enclosure 170 that houses and interconnects a plural number N of the storage devices 110. Without limitation, the enclosure 170 may include a housing that houses the N storage devices in a rack or other structure such as in a RAID (redundant array of independent discs), distributed object storage system, cloud computing network, etc. Each of the devices 110 is configured to operate as a separate storage compute appliance.

A host device 172 is configured to interact with each of the devices 110 via a single or multiple interfaces 174. As before, the host device 172 may take the form of a server, a controller, a computer, etc., and is contemplated as including at least one programmable host processor 176 and host local memory 178.

In the example of FIG. 9, summary results data 180 may be individually generated by each of the storage compute appliances and stored in the host memory 178. The data may be aggregated or further processed by an aggregator application 182 executed by the host processor 176. While the diagram in FIG. 9 indicates each storage compute appliance processes the data stored to its own NVM, it will be recognized that in other embodiments encrypted data sets may be forwarded from one appliance to the next for processing. Suitable embedded encryption keys and other control values can be provided to ensure no side channel data leakage occurs during the analysis.

Different levels of authorized user access can be provided based on different inputs. For example, a first authorized user (AUTH USER 1) is allowed to activate the storage compute process but only receive a first level of output summary results data. A second authorized user (AUTH USER 2) is allowed to receive a second, greater amount of summary results data (e.g., full access v. limited access). Individual data owners and other authorized administrative personnel can gain access to the individual data sets.

Figure 10:
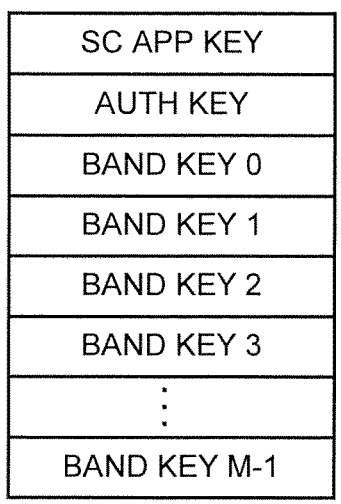
FIG. 10 illustrates a keystore of the storage compute appliance in some embodiments.

FIG. 10 is a depiction of the keystore 132 of the SSD 110 in some embodiments. Other arrangements can be used. The keystore 132 includes a storage compute appliance key 184, an optional authorized (AUTH) user key 186, and respective band keys 188 for bands 0 to M-1. As noted above, the appliance key 184 is used to encrypt the data sets based on a particular application so that all of the data sets analyzed by the application are encrypted. Additional levels of encryption can be supplied, such as at an owner (band key) level and authorized user (auth key) level, but such are merely illustrative and not required.

It follows that, when multiple layers of encryption are applied to the data, the input user data will first be encrypted using the user (band) key, followed by the application key and then, as required, the authorized user key. Decryption of the data will follow in reverse order. The storage compute processor can be configured to apply the necessary decryption to transfer the individual user data sets during normal, non-storage compute related data transfers. Should a user or other authorized party change an encryption key at the data level, the keystore will be updated to reflect the new key(s).

Figure 11:
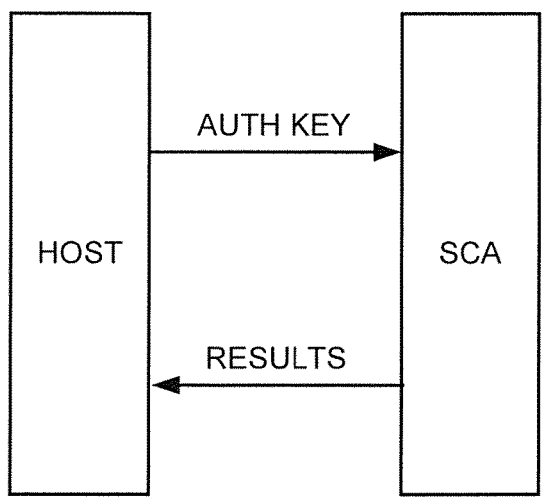
FIG. 11 shows a data exchange operation between a host device and a storage compute appliance in further embodiments.

FIG. 11 shows the host 120 communicating with a selected one of the storage compute appliances 110 discussed above. In this embodiment, the appropriate auth key is supplied along with a suitable execution command from the host to initiate the storage compute process and the generation of the summary results.

Figure 12:
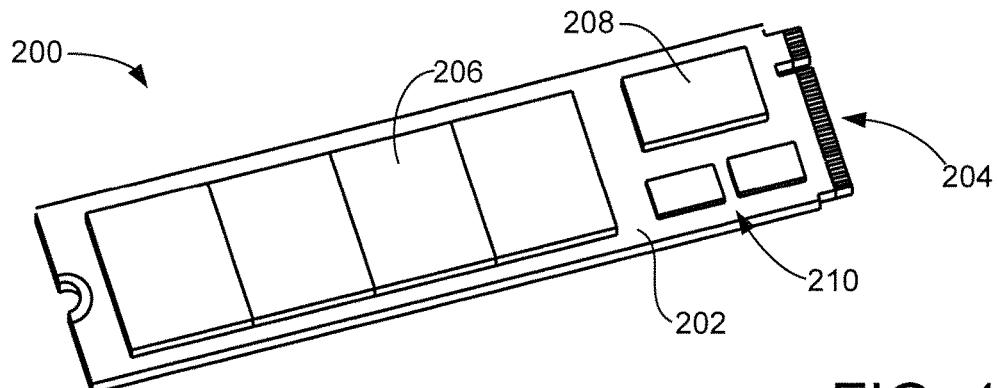
FIG. 12 is an isometric representation of a solid state drive (SSD) that can be configured as a storage compute appliance in accordance with some embodiments.

The embodiments discussed thus far have contemplated the data storage device with the storage compute functionality as corresponding to an SSD. FIG. 12 illustrates an SSD 200 similar to those discussed above that can be provided with such storage compute functionality. The SSD 200 is a plug-in module conforming to the M.2 SSD form factor standard.

The SSD 200 uses non-volatile NAND flash as the NVM, although other forms of memory can be used including and not limited to NOR flash, EEPROM, STRAM, PCRAM, RRAM, etc. The SSD 200 includes a base printed circuit board (PCB) 202 with an edge connector 204 to communicate with an associated host via a host interface. NAND flash memory integrated circuits are denoted at 206, and an SOC 208 serves as the top level controller circuit that incorporates the various controller circuitry of FIGS. 2 and 3, including the storage compute processor. Additional circuits, such as the DRAM, hardware encryption engine, etc. are generally represented by additional control circuit devices 210.

Figure 13:
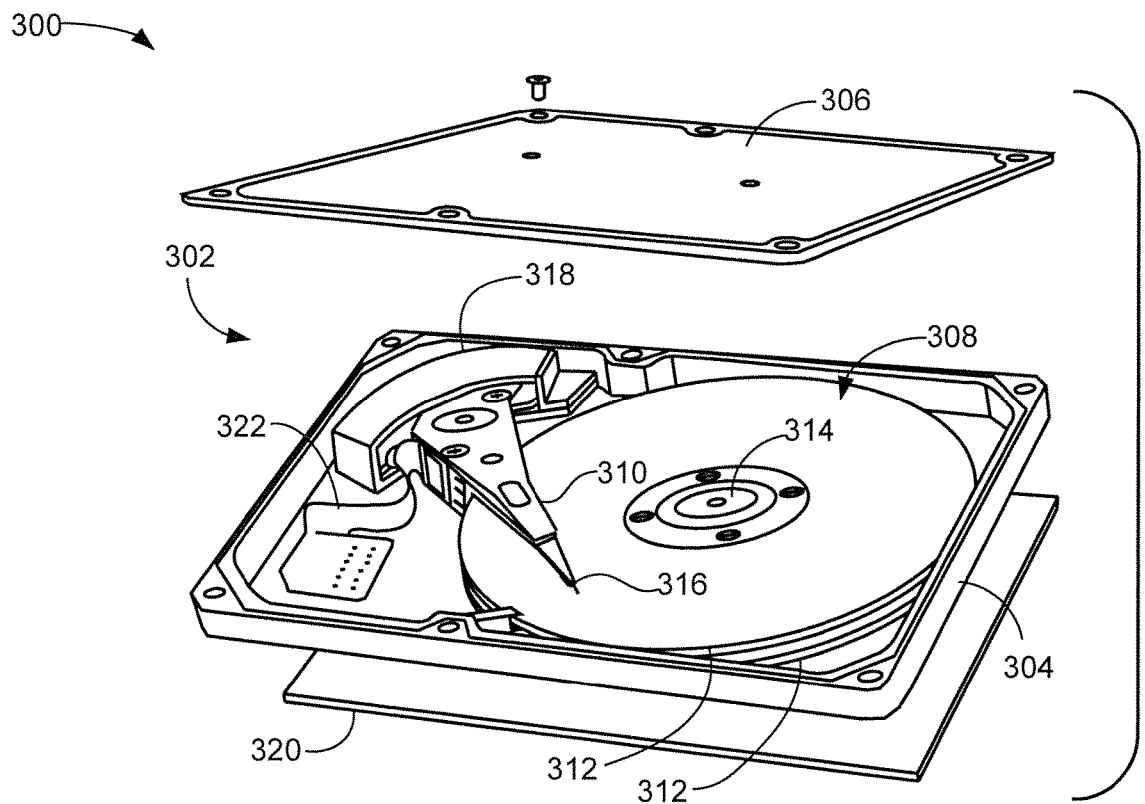
FIG. 13 is an isometric, exploded representation of a hard disc drive (HDD) or hybrid drive that can be configured as a storage compute appliance in accordance with some embodiments.

Other forms of data storage devices can be configured as storage compute appliances as well. FIG. 13 shows a data storage device 300 configured as a hard disc drive (HDD) or a hybrid drive with storage compute functionality as discussed above. As will be recognized, utilizes rotatable data recording media (discs) as the NVM store. A hybrid drive can use rotatable discs as well as another form of NVM memory, such as NAND flash.

The drive 300 includes an environmentally sealed housing 302 formed of a base deck 304 and top cover 306. Housed within the interior of the housing 302 is a disc stack 308 accessed by a rotary actuator 310. The disc stack includes a number of rotatable magnetic recording discs 312 (in this case, two) that are rotated at a constant high velocity by a spindle motor 314. The actuator 310 supports an array of data read/write transducers (heads) 316 adapted to write data to and read data from sectors arranged along concentric data tracks (not shown).

The actuator 310 is pivoted to advance the transducers 316 radially across the disc surfaces using a voice coil motor (VCM) 318. Control electronics, including circuitry corresponding to the controller 102 in FIG. 1 and the storage compute processor 128 in FIG. 3 are supported on an externally mounted printed circuit board (PCB) 320. A flex circuit assembly 322 includes a bulkhead connector to enable the communication of power and data signals between the interior of the device and the external PCB.

From this it can be seen that the storage compute functionality disclosed herein is memory agnostic, both as to form of the NVM as well as to the total storage capacity of the NVM. Generally, any individually addressable data storage device with NVM, a suitable controller circuit and a host interface can be configured to perform the storage compute processing of the present disclosure.

It will now be appreciated that the various embodiments can provide a number of benefits. Individual data sets can be stored and protected for individual users/hosts/owners on a shared (common) data storage device. The data sets can further be protected by one or more appliance level key(s) that encrypt the data sets and which are used to locally decrypt the data within the storage device to perform analyses across the data sets, allowing summary results data to be provided to an authorized user without key or data leakage. The appliance key is referred to as a common or shared key since the key is applied to all of the data sets evaluated by the storage compute process.

The user data sets may be supplied to the storage compute appliance by the various owner(s) of the data sets in encrypted or unencrypted form as desired, and may be returned to the owner(s) in encrypted or unencrypted form. While it is contemplated that the storage compute appliance will maintain in the keystore all required owner level and appliance level encryption keys necessary to unlock and access the data sets, in other embodiments decryption keys at the owner level (or authorized user level) can be supplied to the appliance. However, it will be appreciated that at least the appliance level encryption key or keys will be maintained in a hidden, embedded location within the storage device to prevent or reduce the ability of an attacker from accessing the key and hence, the data. It follows that the appliance level key or keys are not transmitted outside of the device such as via the host interface.

It is to be understood that even though numerous characteristics and advantages of various embodiments of the present disclosure have been set forth in the foregoing description, together with details of the structure and function of various embodiments, this detailed description is illustrative only, and changes may be made in detail, especially in matters of structure and arrangements of parts within the principles of the present disclosure to the full extent indicated by the broad general meaning of the terms in which the appended claims are expressed.

What is claimed is:

1. An apparatus comprising:
a non-volatile memory (NVM) configured to store a plurality of data sets each associated with a corresponding plurality of users of the NVM and each encrypted by at least one encryption key, the plurality of data sets comprising underlying data and personally identifying information each associated with each of the plurality of users; and
a controller circuit configured to direct a data transfer of the data sets between the NVM and a host device via a host interface, the controller circuit comprising a storage compute appliance processor circuit configured to perform a storage compute appliance process by using the at least one encryption key to decrypt the data sets to provide a corresponding plurality of decrypted data sets in an internal local memory, executing a storage compute application to generate summary results data from the decrypted data sets of the plurality of users, and to transfer the summary results data across the host interface to an authorized user without a corresponding transfer of any portion of the underlying data and without a corresponding transfer of any portion of the personally identifying information of the plurality of users to the authorized user.

2. The apparatus of claim 1, wherein the storage compute appliance process further comprising storing an encrypted copy of the summary results data to the NVM with corresponding time stamp information associated with a time of the generation of the summary results data.

3. The apparatus of claim 1, characterized as a solid state drive (SSD) configured as a storage compute appliance, wherein the NVM comprises NAND flash memory.

4. The apparatus of claim 1, characterized as a hard disc drive (HDD) or a hybrid drive configured as a storage compute appliance, wherein the NVM comprises at least one rotatable data recording medium.

5. The apparatus of claim 1, wherein the internal local memory comprises volatile memory, and the storage compute appliance processor circuit is further configured to jettison the decrypted data sets from the internal local memory after the transfer of the summary results data to the authorized user across the host interface.

6. The apparatus of claim 1, wherein the NVM is a shared NVM so that each data set of the plurality of data sets has a different owner from among the plurality of users and is separately encrypted by a different encryption key, and wherein all of the data sets are further encrypted using a common appliance encryption key.

7. The apparatus of claim 1, wherein the data sets comprise confidential data associated with each of the plurality of users and the summary results data does not include any of the confidential data.

8. The apparatus of claim 7, wherein the confidential data comprises medical records and the storage compute appliance process evaluates the medical records of the plurality of users.

9. The apparatus of claim 7, wherein the confidential data comprises image data and the storage compute appliance process evaluates the image data of the plurality of users without transferring the image data with the summary results data.

10. The apparatus of claim 1, characterized as a data storage device configured to communicate with a host device via the host interface, the host device comprising a programmable processor and associated programming to aggregate the summary results data from the data storage device.

11. A method comprising:
  encrypting each of a plurality of data sets using at least one encryption key to generate encrypted data sets, each of the data sets owned by a different user of a plurality of users;
  storing the encrypted data sets to a non-volatile memory (NVM) having a controller circuit configured to transfer the plurality of data sets between the NVM and a host device using a host interface;
  performing a storage compute process using the controller circuit by using the at least one encryption key to decrypt the encrypted data sets to provide a corresponding plurality of decrypted data sets in an internal local memory, generating summary results data from the decrypted data sets in the internal local memory, and transferring the summary results data across the host interface to an authorized user without a corresponding transfer of any portion of the plurality of data sets across the host interface to the authorized user, the summary results combining data from multiple ones of the plurality of users; and
  storing a copy of the summary results data, encrypted by the at least one encryption key, to the NVM in conjunction with time stamp information associated with the storage compute process.

12. The method of claim 11, wherein the storage compute process is a first storage compute process carried out at a first time by a first authorized user to generate first summary results data for a first subset of the encrypted data sets stored in the NVM, wherein the method further comprises performing a different, second compute process carried out at a different, second time by a different, second authorized user for a different, second subset of the encrypted data sets stored in the NVM to generate different, second summary results data, and wherein respective first and second time stamp information associated with the first and second times are stored to the NVM.

13. The method of claim 11, wherein the plurality of data sets comprise confidential patient records associated with each of the plurality of users, and wherein the summary results data constitutes a correlation study of the patient records without disclosing any portion of the patient records.

14. The method of claim 11, wherein the NVM comprises a combined memory from each of a plurality of data storage devices in a data storage array.

15. The method of claim 11, wherein the NVM is a shared NVM so that each data set of the plurality of data sets has a different owner and is separately encrypted by a different encryption key supplied by the associated owner, wherein all of the data sets are further encrypted using a common appliance encryption key which remains internal to the controller circuit, and wherein the summary results data includes an evaluation of each of the data sets from each of the different owners.

16. The method of claim 11, wherein the NVM is partitioned into a plurality of bands each having an associated total data storage capacity, wherein the data sets in each band are encrypted by a different band encryption key, wherein each of the data sets in all of the bands are further encrypted using a common appliance encryption key, and wherein the storage compute process comprises sequentially decrypting the data sets using the band keys and the appliance encryption key using an encryption engine of at least one data storage device.

17. The method of claim 11, wherein the encrypted data sets comprise personally identifying information and underlying data associated with each of the plurality of users, and wherein the summary results data does not include any of the personally identifying information or the underlying data.

18. A system comprising:
  a plurality of data storage devices arranged in an array to form a consolidated non-volatile memory (NVM) to which data sets are stored in an encrypted form from a plurality of users, the data sets including underlying data and personally identifying information associated with each of the plurality of users;
  a storage compute processor having associated programming in a storage compute processor memory to sequentially decrypt and transfer the data sets from the NVM to the storage compute processor memory, to generate summary data associated with the decrypted and transferred data sets that excludes the personally identifying information and the underlying data, to transfer the summary data to a requesting user, to store a copy of the summary data to the NVM with a corresponding time stamp, and to jettison the decrypted and transferred data sets and the summary data from the storage compute processor memory.

19. The system of claim 18, wherein the copy of the summary data stored to the NVM is encrypted using a selected encryption key.

20. The system of claim 18, wherein the particular user is a first user having authorization to obtain a first summary data report corresponding to a subset of the data sets in the NVM, and the storage compute processor further has associated programming in the storage compute processor memory to obtain a second summary data report corresponding to all of the data sets in the NVM.

* * * * *